United States Patent
Ali et al.

(10) Patent No.: US 8,252,825 B2
(45) Date of Patent: Aug. 28, 2012

(54) ANGIOTENSIN II RECEPTOR ANTAGONISTS

(75) Inventors: Amjad Ali, Freehold, NJ (US); Michael Man-Chu Lo, Edison, NJ (US); Christopher Franklin, Quincy, NJ (US); Nicoletta Almirante, Milan (IT); Silvia Stefanini, San Donato Milanese (IT); Laura Storoni, Cesano Maderno (IT); Stefano Biondi, Pero (IT); Ennio Ongini, Segrate (IT)

(73) Assignees: NicOx, Milan (IT); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/743,402

(22) PCT Filed: Nov. 21, 2008

(86) PCT No.: PCT/US2008/012984
§ 371 (c)(1),
(2), (4) Date: May 18, 2010

(87) PCT Pub. No.: WO2009/070241
PCT Pub. Date: Jun. 4, 2009

(65) Prior Publication Data
US 2010/0273845 A1 Oct. 28, 2010

Related U.S. Application Data

(60) Provisional application No. 61/137,697, filed on Aug. 1, 2008, provisional application No. 61/004,320, filed on Nov. 26, 2007.

(51) Int. Cl.
*A61K 31/4184* (2006.01)
*A61K 31/4178* (2006.01)
*C07D 403/10* (2006.01)
*A61P 9/12* (2006.01)

(52) U.S. Cl. .................................. 514/381; 548/253
(58) Field of Classification Search .................. None
See application file for complete search history.

(56) References Cited

U.S. PATENT DOCUMENTS
7,834,042 B2 * 11/2010 Sebhat et al. ............... 514/381
2008/0194660 A1 * 8/2008 Sebhat et al. ............... 514/381
2010/0152259 A1 * 6/2010 Sebhat et al. ............... 514/381

FOREIGN PATENT DOCUMENTS
WO WO2005/011646 A3 2/2005
WO WO2005/023182 A3 3/2005

OTHER PUBLICATIONS
WO2009/070241 A3—Search Report; Completed—Apr. 6, 2009; Searching authority—The European Patent Office; Performed by authorized Officer—Damian Grassi.

* cited by examiner

Primary Examiner — Sun Jae Loewe

(57) ABSTRACT

A compound having the structure

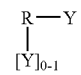

wherein R is an angiotensin receptor antagonist active group, and Y is
1) —$(CH_2)_3R^5$,
2) —$C(O)(CH_2)_2R^5$,
3) —$C(R^1R^2)OC(O)O(CH_2)_nR^5$, wherein n is 1 or 2,
4) —$C(R^1R^2)OC(O)CH_2CH_2R^5$,
5) —$C(R^1R^2)OC(O)OCH_2CH_2C(R^3R^4)R^5$,

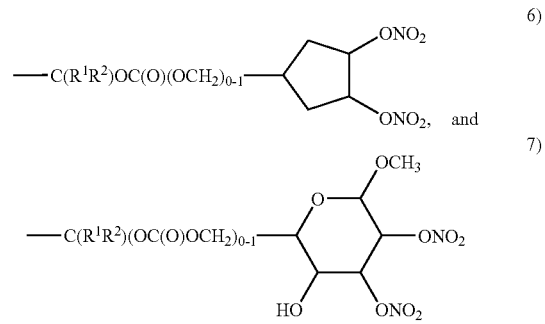

provided that when Y is —$C(O)(CH_2)_2R^5$, then R is

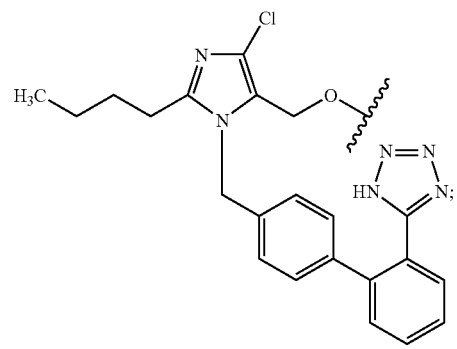

$R^1$, $R^2$, $R^3$ and $R^4$ are independently selected from the group consisting of hydrogen and $C_{1-4}$ alkyl;
$R^5$ is —$CH(ONO_2)CH(ONO_2)R^6$;
$R^6$ is selected from $CH_3$, $CH_2CH_3$ and $CH(CH_3)_2$;
or a pharmaceutically acceptable salt or hydrate thereof, which is useful for treating hypertension.

3 Claims, No Drawings

ANGIOTENSIN II RECEPTOR ANTAGONISTS

CROSS REFERENCE TO RELATED APPLICATIONS

This application is a U.S. National Phase application under 35 U.S.C. §371 of PCT Application No. PCT/US2008/012984 filed Nov. 21, 2008, which claims priority under 35 U.S.C. §119(e) from U.S. Provisional Application No. 61/137,697 filed Aug. 1, 2008 and U.S. Provisional Application No. 61/004,320 filed Nov. 26, 2007.

BACKGROUND OF THE INVENTION

U.S. Pat. No. 5,138,069 generically and specifically describes 2-butyl-4-chloro-1-[p-(o-1H-tetrazol-5-ylphenyl)-benzyl]imidazole-5-methanol potassium salt and 2-butyl-4-chloro-1-[(2'-1H'-tetrazol-5-yl)biphenyl-4-yl)methyl]imidazole-5-carboxylic acid. Columns 261-263 of U.S. Pat. No. 5,136,069 describe general procedures for formulating compounds described in the patent, including capsules, tablets, injection formulations, and suspensions. U.S. Pat. No. 5,153,197, describes the use of these compounds, alone and in combination with a diuretic, to treat a patient having hypertension.

WO2005011646 describes angiotensin II receptor blocker nitroderivatives, pharmaceutical compositions containing them and their use for the treatment of cardiovascular, renal and chronic liver diseases, inflammatory processes and metabolic syndromes. The publication describes a variety of angiotensin receptor blocker compounds each of which are covalently linked in a variety of ways to a nitric oxide group. Specific examples include angiotensin receptor blockers with one covalently-linked nitric oxide group, and angiotensin receptor blockers with two independently-covalently-linked nitric oxide groups. WO2005023182 describes nitrosated and nitrosylated cardiovascular compounds, and compositions comprising at least one nitrosated and nitrosylated cardiovascular compound and optionally at least one nitric oxide donor. The cardiovascular compound which is nitrosated or nitrosylated may be an aldosterone antagonist, an angiotensin II receptor antagonist, a calcium channel blocker, an endothelin antagonist, a hydralazine compound, a neutral endopeptidase inhibitor or a renin inhibitor. The nitric oxide donor may be selected from S-nitrosothiols, nitrites, nitrates, N-oxo-N-nitrosamines, furoxans, and sydnonimines.

WO2005070868 describes combination therapy for treating cyclooxygenase-2 mediated diseases or conditions at risk of thrombotic cardiovascular events which involves administering selected cyclooxygenase-2 inhibitor in combination with a nitric oxide donating compound such as 5,6-bis(nitrooxy)hexyl acetate, 6-hydroxyhexane-1,2-diyl dinitrate, 5-hydroxypentane-1,2-diyl dinitrate, (5R)-5,6-bis(nitrooxy) hexyl 4-nitrobenzoate, (5S)-5,6-bis(nitrooxy)hexyl 4-nitrobenzoate, (2R)-6-hydroxyhexane-1,2-diyl dinitrate, (2S)-6-hydroxyhexane-1,2-diyl dinitrate, (2S)-propane-1,2-diyl dinitrate, and (2R)-propane-1,2-diyl dinitrate.

SUMMARY OF THE INVENTION

The present invention includes angiotensin II receptor antagonist bis(nitrooxy) derivatives, including 2-butyl-4-chloro-1-[(2'-(1-H-tetrazol-5-yl)biphenyl-4-yl)methyl]-imidazole-5-carboxylate bis(nitrooxy) derivatives, including various pharmaceutically acceptable salts and hydrates of these forms, and pharmaceutical formulations for controlled and sustained delivery of these forms to a patient.

The salts include non-toxic salts such as those derived from inorganic acids, e.g. hydrochloric, hydrobromic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, by administering an angiotensin II receptor antagonist of the invention to a patient having one or more of these conditions.

DETAILED DESCRIPTION OF THE INVENTION AND PREFERRED EMBODIMENTS

Compounds of the invention are angiotensin II receptor antagonist bis(nitrooxy) derivatives having the general formula:

wherein R is selected from the group consisting of

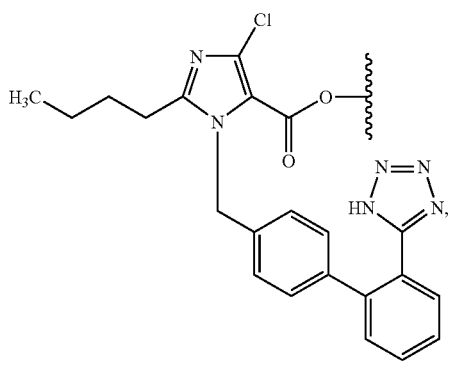

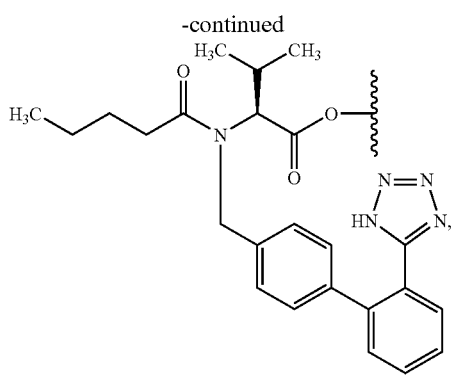
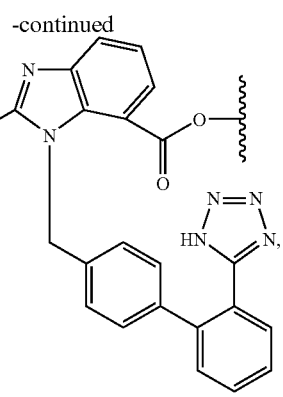
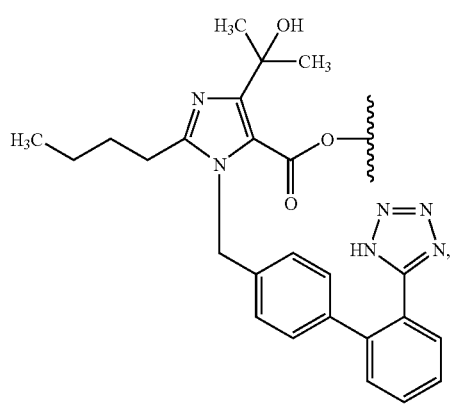
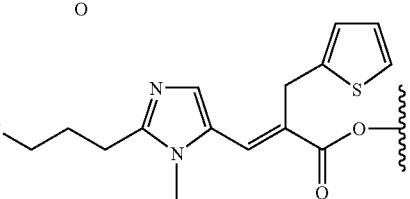
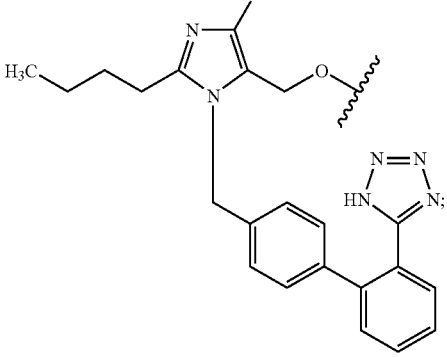
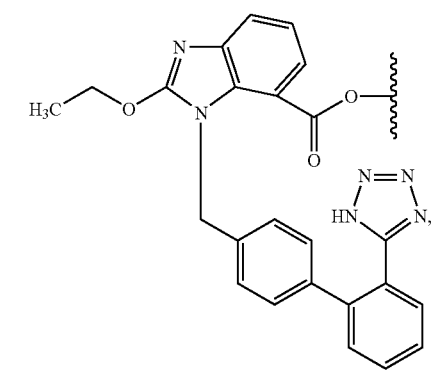
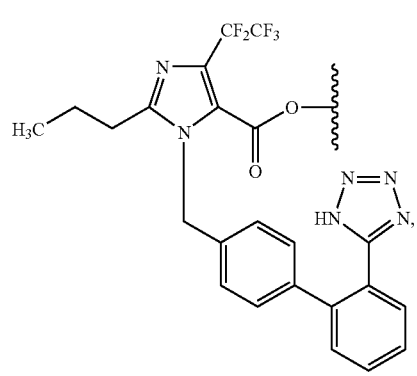
Y is selected from the group consisting of
1) —(CH$_2$)$_3$R$^5$,
2) —C(O)(CH$_2$)$_2$R$^5$,
3) —C(R$^1$R$^2$)OC(O)O(CH$_2$)$_n$R$^5$, wherein n is 1 or 2,
4) —C(R$^1$R$^2$)OC(O)CH$_2$CH$_2$R$^5$,
5) —C(R$^1$R$^2$)OC(O)OCH$_2$CH$_2$C(R$^3$R$^4$)R$^5$,

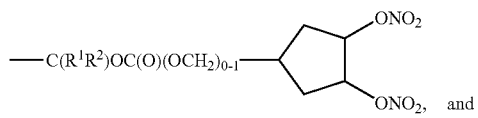 6)

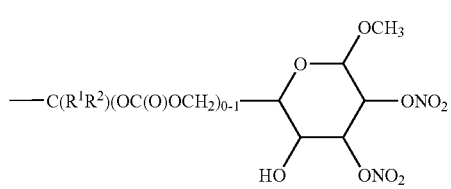 7)

provided that when Y is —C(O)(CH$_2$)$_2$R$^5$, then R is

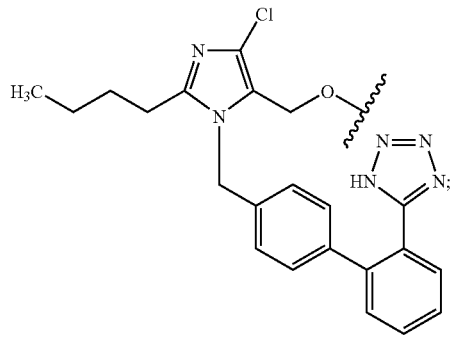

R$^1$, R$^2$, R$^3$ and R$^4$ are independently selected from the group consisting of hydrogen and C$_{1-4}$ alkyl;

R$^5$ is —CH(ONO$_2$)CH(ONO$_2$)R$^6$

R$^6$ is selected from CH$_3$, CH$_2$CH$_3$ and CH(CH$_3$)$_2$, or a pharmaceutically acceptable salt thereof.

In one embodiment, R$^1$ is CH$_3$ and R$^2$ is H or CH$_3$ and all other variables are as previously defined.

In another embodiment, R$^3$ is CH$_3$ or H and R$^4$ is H, and all other variables are as previously defined.

In another embodiment, R is selected from the group consisting of

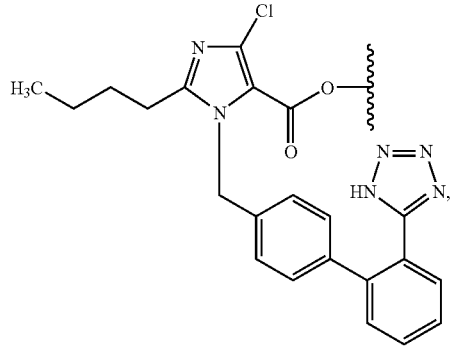

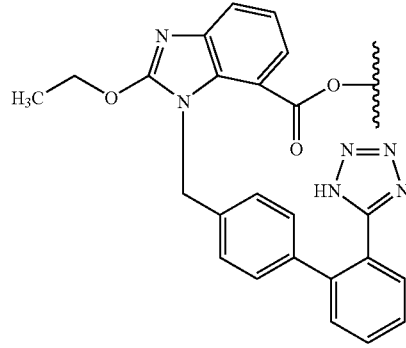

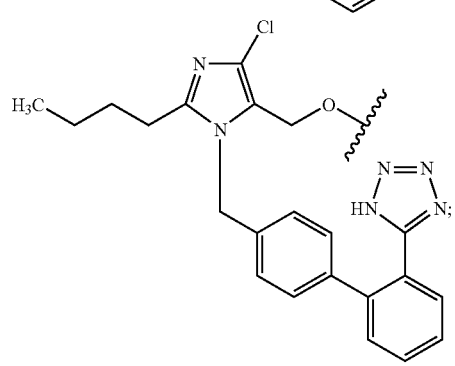

and all other variables are as previously defined.

In another embodiment. R$^5$ is selected from the group consisting of

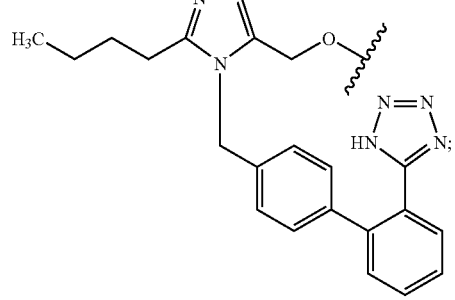

and all other variables are as previously defined.

In another embodiment, R$^5$ is selected from the group consisting of

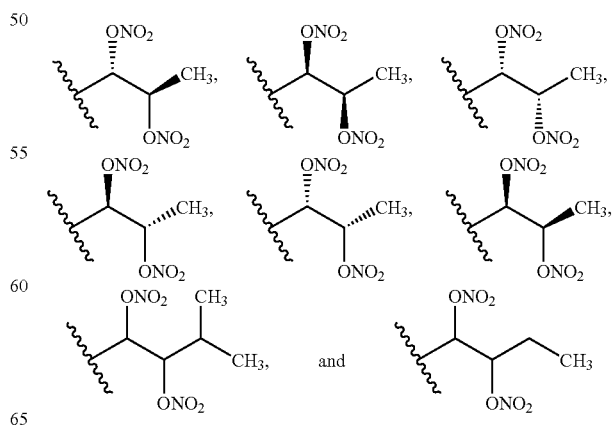

and all other variables are as previously defined.

In another embodiment, the compound is selected from the group of compounds shown below:
TABLE (i)-(xi)
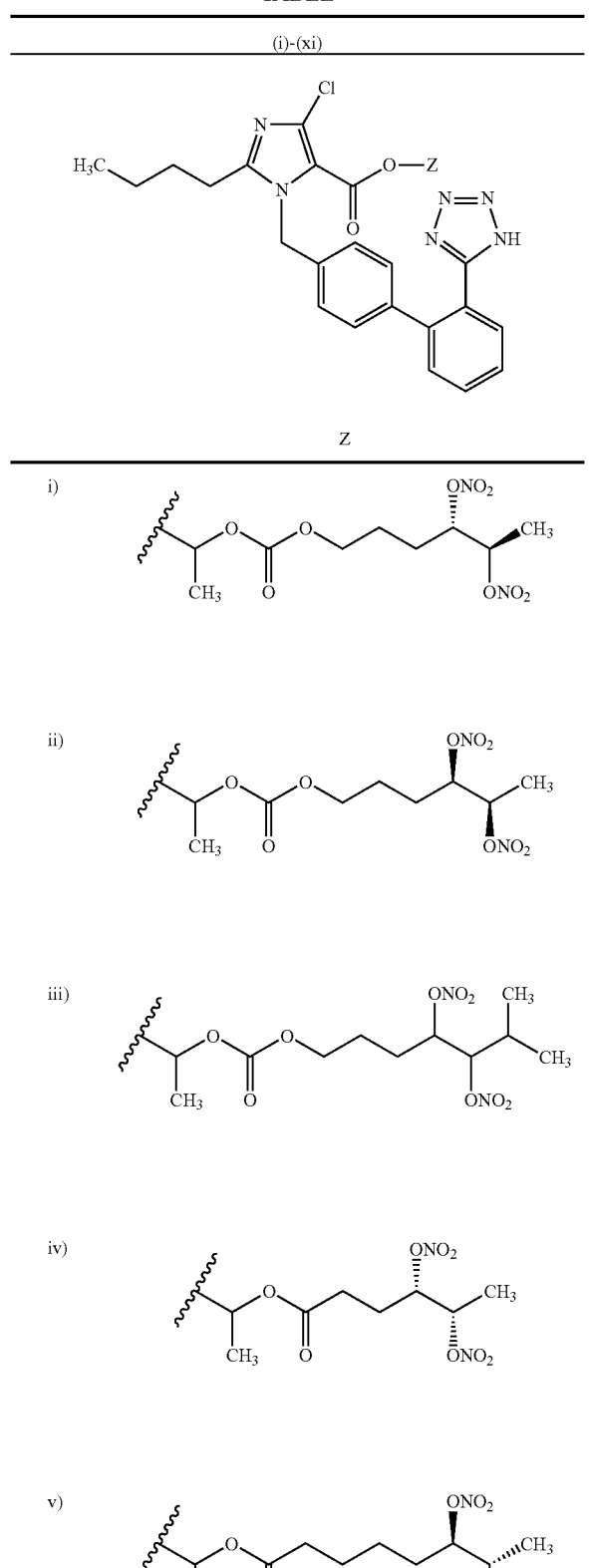
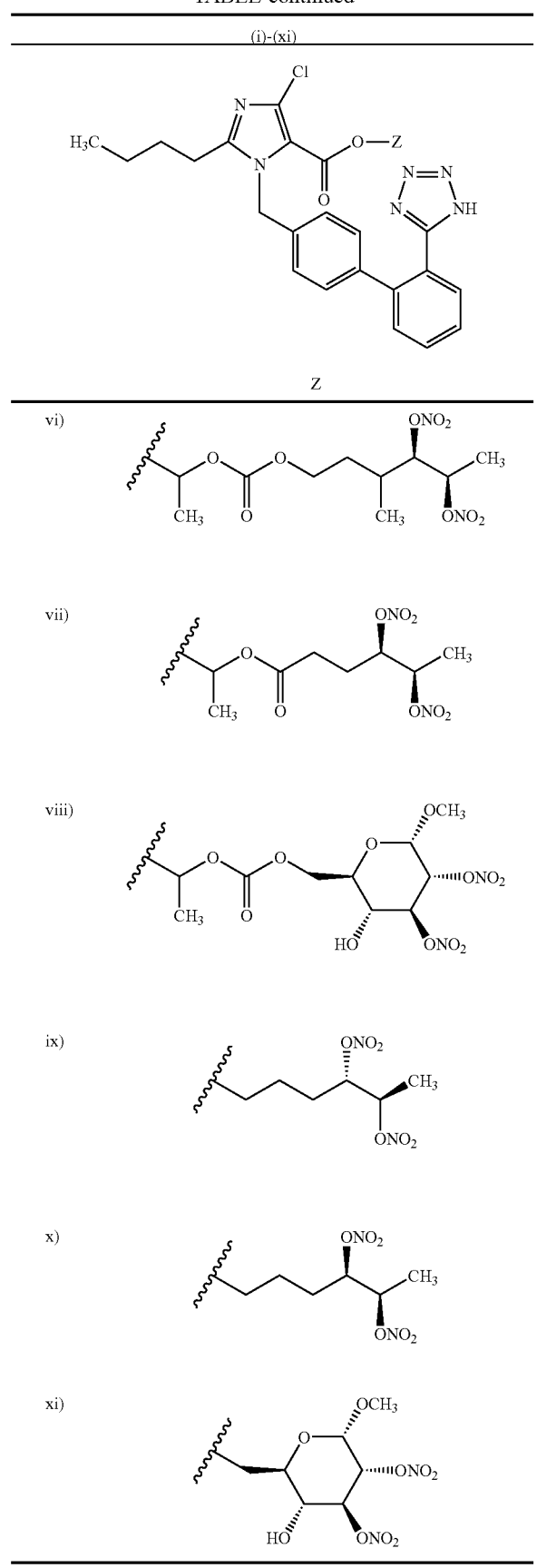

TABLE (xii)-(xxvii)
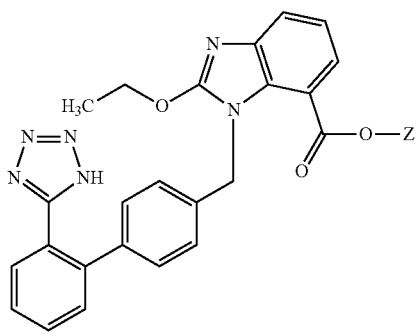
| Z | |
|---|---|
| xii) | 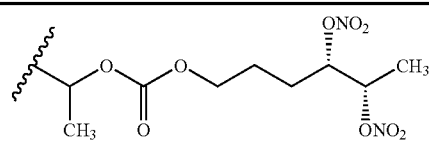 |
| xiii) | 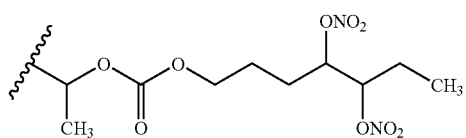 |
| xiv) | 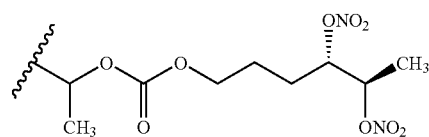 |
| xv) | 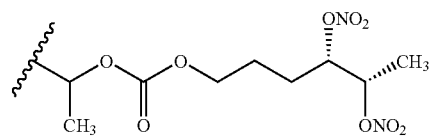 |
| xvi) | 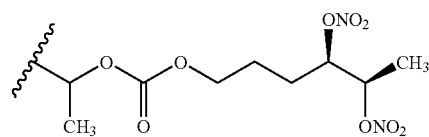 |
| xvii) | 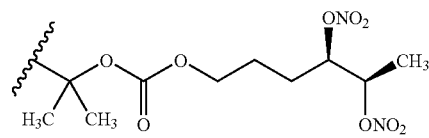 |
| xviii) | 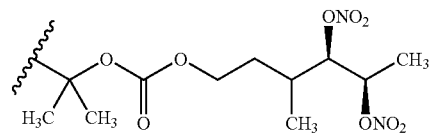 |
| xix) | 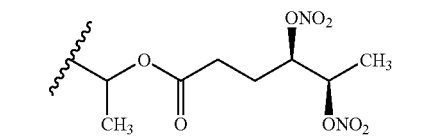 |
TABLE-continued (xii)-(xxvii)
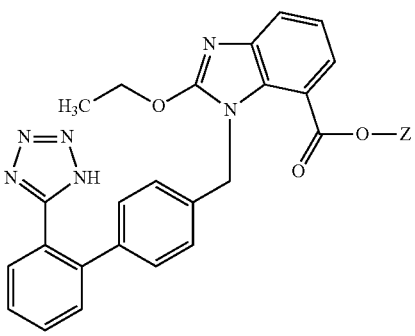
| Z | |
|---|---|
| xx) | 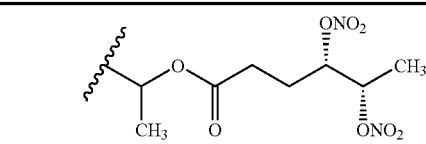 |
| xxi) | 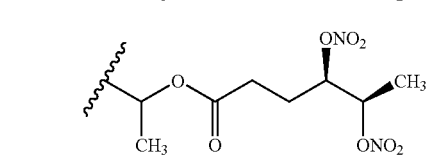 |
| xxii) | 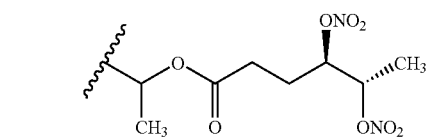 |
| xxiii) | 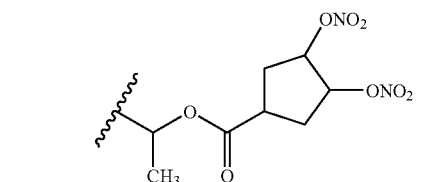 |
| xxiv) | 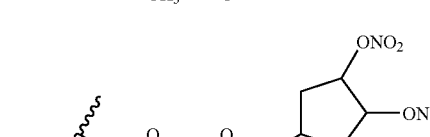 |
| xxv) | 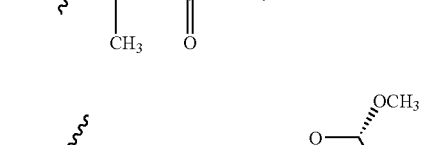 |
| xxvi) | 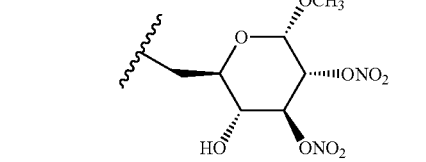 |

TABLE-continued (xii)-(xxvii)

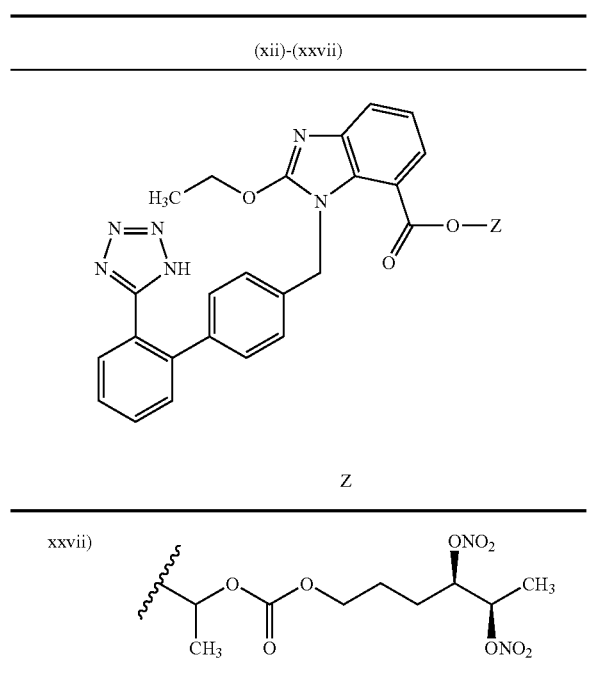

Z xxvii)

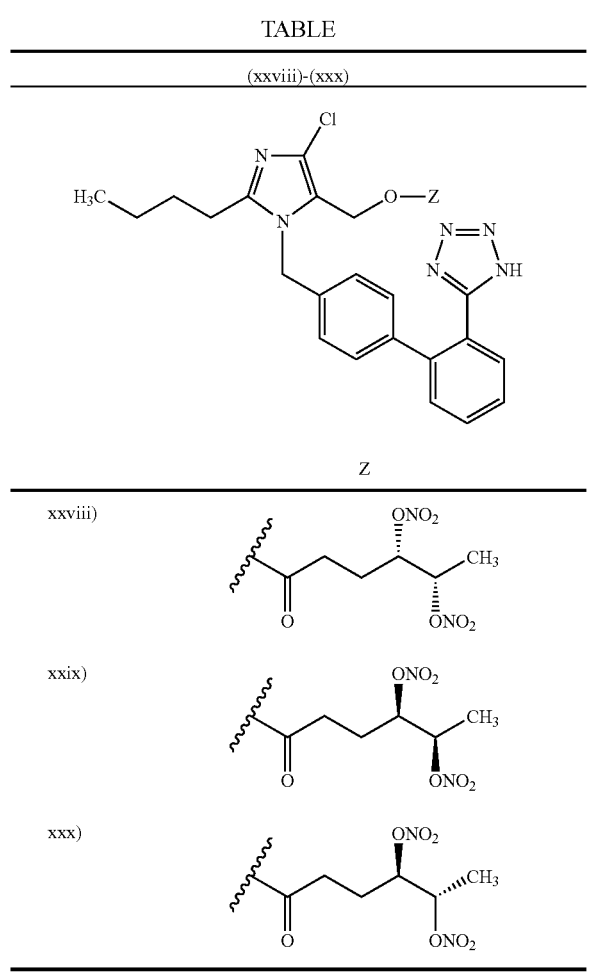

TABLE (xxviii)-(xxx)

xxviii)

xxix)

xxx)

In another embodiment, the compound has the structure

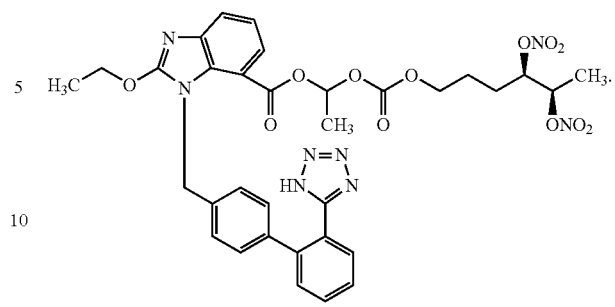

In another embodiment, the compound has the structure

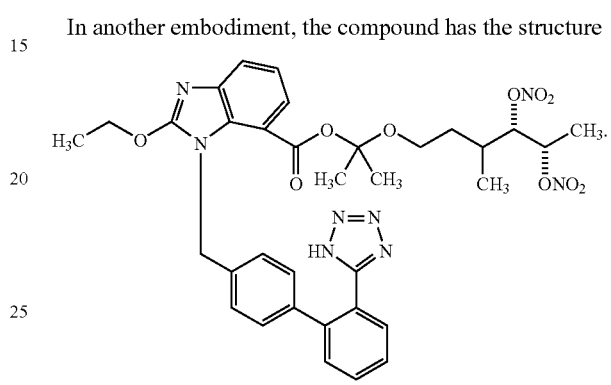

In another embodiment, the compound has the structure

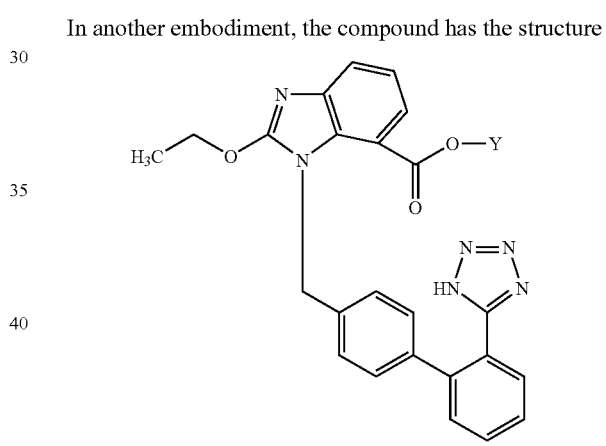

wherein
Y is —C(R$^1$R$^2$)OC(O)OCH$_2$CH$_2$C(R$^3$R$^4$)R$^5$;
R$^1$ and R$^2$ are CH$_3$;
R$^3$ and R$^4$ are independently selected from the group consisting of hydrogen and C$_{1-4}$ alkyl;
R$^5$ is —CH(ONO$_2$)CH(ONO$_2$)R$^6$; and
R$^6$ is selected from CH$_3$, CH$_2$CH$_3$ and CH(CH$_3$)$_2$.

The compounds of the present invention may have one or two chiral centers, providing for up to two ((R) and (S)) or four (R,R), (S,S), (R,S), and (S,R) stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. The structure marking "*" indicates the location of a carbon atom that is a chiral center.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or CH$_3$ or a symbol that is an extended bond as the terminal group e.g. 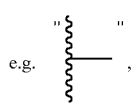, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

Compounds 1 and 2 shown below were studied for systolic blood pressure lowering when orally administered to conscious telemetered dogs. Compared to Compound 1, Compound 2 provided extended peak effect and duration of action at the same dose (10 mg/kg) (see Data Table 1).

DATA TABLE 1

| | Approximate change in systolic blood pressure (mmHg) | | |
|---|---|---|---|
| | 1-6 h | 6-12 h | 12-18 h |
| Compound 1 | −14 | −7 | 3 |
| Compound 2 | −23 | −11 | −2 |

Vessel Relaxation

The ability of the compounds to induce vasorelaxation was tested in vitro in isolated rabbit thoracic aorta preparations (Wanstall J. C. et al., Br. J. Pharmacol., 134:463-472, 2001). Male New Zealand rabbits were anaesthetized with thiopental-Na (50 mg/kg, iv), sacrificed by exsanguinations and then the thorax was opened and the aorta dissected. Aortic ring preparations (4 mm in length) were set up in physiological salt solution (PSS) at 37° C. in small organ chambers (5 ml). The composition of PSS was (mM): NaCl 130, $NaHCO_3$ 14.9, $KH_2PO_4$ 1.2, $MgSO_4$ 1.2, HEPES 10, $CaCl_2$, ascorbic acid 170 and glucose 1.1 (95% $O_2$/5% $CO_2$; pH 7.4). Each ring was mounted under 2 g passive tension. Isometric tension was recorded with a Grass transducer (Grass FT03) attached to a BIOPAC MP150 System. Preparations were allowed to equilibrate for 1 h, and then contracted submaximally with noradrenaline (NA, 1 μM) and, when the contraction was stable, acetylcholine (ACh, 10 μM) was added. A relaxant response to ACh indicated the presence of a functional endothelium. Vessels that were unable to contract NA or showed no relaxation to ACh were discarded. When a stable precontraction was reached, a cumulative concentration-response curve to either of the vasorelaxant agents was obtained in the presence of a functional endothelium. Each arterial ring was exposed to only one combination of inhibitor and vasorelaxant. Moreover, the effect of the soluble guanylyl cyclase inhibitor ODQ (1-H-(1,2,4)-oxadiazol(4,3-a)quinoxalin-1-one) on vasorelaxation elicited by the compounds was examined preincubating the aortic rings with ODQ (10 μM) for 20 min.

Example 3 and 4 were evaluated for vessel relaxation. In vitro, tissue-based measure of vessel relaxation, determined in rabbit aortic slices, demonstrated vessel relaxation according to the indicated $EC_{50}$ (molar concentration of compound which produces 50% of the maximum possible response for that compound—Data Table 2).

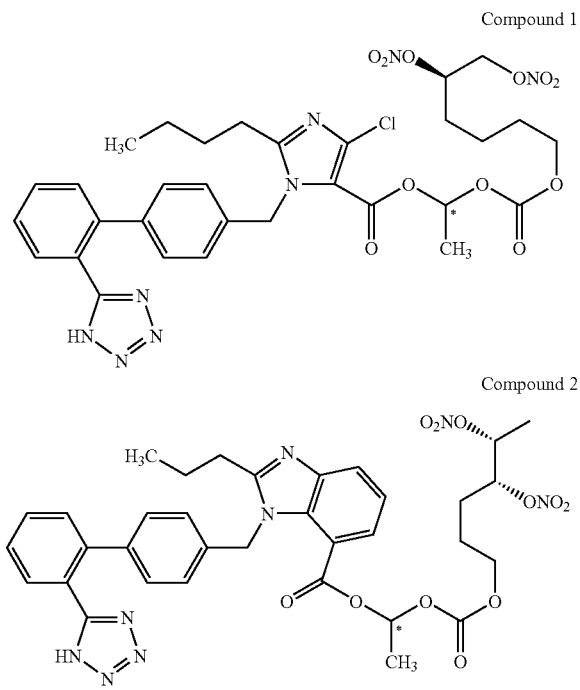

Compound 1

Compound 2

DATA TABLE 2

| Structure | Compound Number | $EC_{50}$ in vessel relaxation assay |
|---|---|---|
| 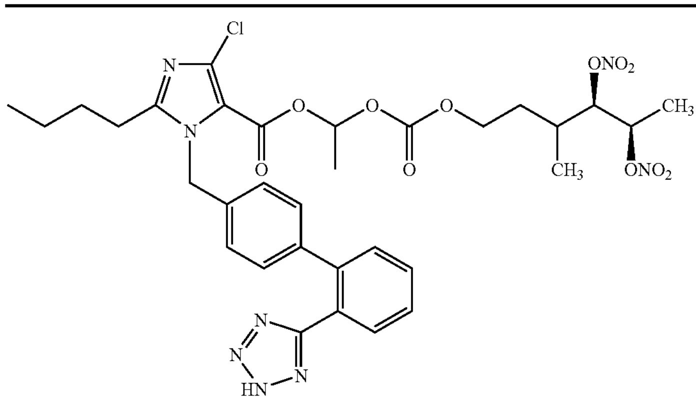 | Example 3 | 8.5 μM |

DATA TABLE 2-continued

| Structure | Compound Number | EC$_{50}$ in vessel relaxation assay |
|---|---|---|
| 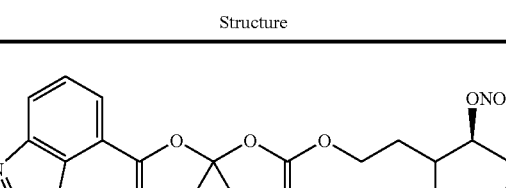 | Example 4 | 6.4 μM |

The angiotensin II receptor antagonists of the invention are useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system.

The angiotensin II receptor antagonists of the invention are especially useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment and/or prophylaxis of diseases, which are associated with a dysregulation of the renin-angiotensin system, in particular to a method for the treatment or prophylaxis of the above-mentioned diseases, said methods comprising administering to a patient a pharmaceutically active amount of an angiotensin II receptor antagonist of the invention.

The invention also relates to the use of angiotensin II receptor antagonists of the invention for the preparation of a medicament for the treatment and/or prophylaxis of the above-mentioned diseases.

The above-mentioned angiotensin II receptor antagonists of the invention are also of use in combination with other pharmacologically active compounds comprising angiotensin converting enzyme inhibitors (e.g. alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S,5S,7S)-N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, verapamil, diltiazem, gallopamil, niludipine, nimodipine, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone)) or with other drugs beneficial for the prevention or the treatment of the above-mentioned diseases including nitroprusside and diazoxide.

The dosage regimen utilizing the angiotensin II receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the angiotensin II receptor antagonists, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the angiotensin II receptor antagonists may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The angiotensin II receptor antagonists of the invention can be administered in such oral forms as tablets, capsules and granules. The angiotensin II receptor antagonists are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose acetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

2-Butyl-4-chloro-1-[(2'-(1-H-tetrazol-5-yl)biphenyl-4-yl) methyl]-imidazole-5-carboxylic acid is the active metabolite of 2-butyl-4-chloro-1-[p-(o-1H-tetrazol-5-ylphenyl)-benzyl] imidazole-5-methanol which is available as a monopotassium salt (also known as losartan potassium salt). Losartan potassium salt is available commercially as the active ingredient in COZAAR® (Merck & Co., Inc. (Whitehouse Station, N.J.)). The preparation of losartan potassium salt is described in U.S. Pat. Nos. 5,138,069, 5,130,439, and 5,310,928. Tetrazolylphenylboronic acid intermediates useful in the synthesis of losartan potassium salt are described in U.S. Pat. No. 5,206,374. Additional patents which describe procedures useful for making losartan include U.S. Pat. Nos. 4,820,843, 4,870,186, 4,874,867, 5,039,814, and 5,859,258.

2-ethoxy-1-{[2'-(1-trityl-1H-tetrazol-5-yl)biphenyl-4-yl] methyl}-1H-benzimidazole-7-carboxylic acid, used as starting material in EXAMPLE 2 and for preparing 1-methyl-1-{[(4-nitrophenoxy)carbonyl]oxy}ethyl 2-ethoxy-1-{[2'-(1-trityl-1H-tetrazol-5-yl)biphenyl-4-yl]methyl}-1H-benzimidazole-7-carboxylate (INTERMEDIATE 4), can be prepared by the method reported in Keiji Kubo et al., Journal of Medicinal Chemistry, 1993, Vol. 36, 2343-2349.

Applying the methods reported in Examples 1-3 but starting from (S)-3-methyl-2-(N-((2'-(2-trityl-2H-tetrazol-5-yl) biphenyl-4-yl)methyl)pentanamido)butanoic acid (trityl valsartan) or 4-(2-hydroxypropan-2-yl)-2-propyl-1-((2'-(2-trityl-2H-tetrazol-5-yl)biphenyl-4-yl)methyl)-1H-imidazole-5-carboxylic acid (trityl olmesartan), the corresponding valsartan and olmesartan esters can be obtained. (S)-3-methyl-2-(N-((2'-(2-trityl-2H-tetrazol-5-yl) biphenyl-4-yl)methyl)pentanamido)butanoic acid (trityl valsartan) can be prepared reacting (S)-2-(N-((2'-(2H-tetrazol-5-yl)biphenyl-4-yl)methyl)pentanamido)-3-methylbutanoic acid (valsartan, U.S. Pat. No. 5,399,578) with trityl chloride as described in INTERMEDIATE 3, Step C for analogous compound.

4-(2-hydroxypropan-2-yl)-2-propyl-1-((2'-(2-trityl-2H-tetrazol-5-yl)biphenyl-4-yl)methyl)-1H-imidazole-5-carboxylic acid (trityl olmesartan) can be obtained according to the method reported in Hiroaki Yanagisawa, Journal of Medicinal Chemistry 1996, 39, 323-338.

Intermediate 1

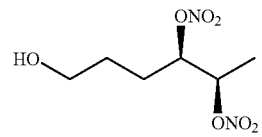

(2R,3R)-6-hydroxyhexane-2,3-diyl dinitrate

The title compound was prepared by following the procedure for examples 4 and 6 in WO2005070868(A1), except that the reagent hex-5-en-1-ol was replaced by (4E)-hex-4-en-1-ol. $^1$H NMR (500 MHz, CDCl$_3$) δ 5.2-5.4 (m, 2H), 3.7-3.8 (m, 2H), 1.66-1.98 (m, 4H), 1.46 (d, J=6.2 Hz, 3H).

Intermediate 2

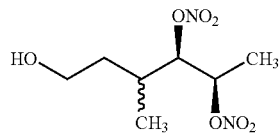

(2R,3R)-6-hydroxy-4-methylhexane2,3-diyl dinitrate

STEP A: 3-methyl-hex-4-en-1-ol

To a solution of 3-methylhex-4-enal (prepared as described by Wei X., et al in *J. Org. Chem.* 2007, 72(11), 4250) (16.5 g, 146 mmol) in ethanol abs. at 0° C., NaBH$_4$ (12.9 g, 175 mmol) was added in 30 minutes. The mixture was stirred at 0° C. for 4 hrs and was quenched with solid ammonium chloride. Water was added and the mixture was extracted with $CH_2Cl_2$. The combined organic layers were dried over $MgSO_4$ and concentrated under reduced pressure. The crude product was distilled at 87-88° C. and obtained as colorless oil.

STEP B: 3-methylhex-4-enyl 4-nitrobenzoate

A solution of freshly crystallized 4-nitrobenzoyl chloride (10.1 g, 54.5 mmol) in $CH_2Cl_2$ (ml 20) was added dropwise to a solution of 3-methyl-hex-4-en-1-ol (5.4 g, 47.5 mmol) and TEA (8.6 ml, 61.8 mmol) in $CH_2Cl_2$ (ml 50) at 0° C. under nitrogen. The mixture was stirred at 0° C. for 1 h and poured in ice/water (100 g). The $CH_2Cl_2$ was separated and the water phase was extracted twice with $CH_2Cl_2$. The combined organic layers were dried over $MgSO_4$ and concentrated under reduced pressure. The crude product was distilled at 171-173° C. 4 mmHg to give the title compound as yellow oil.

Step C: (2R,3R)-6-hydroxy-4-methylhexane-2,3-diyl dinitrate

The title compound was prepared by following the procedure for example 4 in WO2005070868(A1), except that the reagent hex-5-en-1-yl 4-nitrobenzoate was replaced by 3-methylhex-4-enyl 4-nitrobenzoate.
$^1$H NMR (300 MHz, $CDCl_3$) δ 5.38-5.33 (m, 1H), 5.30-5.13 (m, 1H), 3.79-3.59 (m, 2H), 2.27-2.18 (m, 1H), 1.83-1.64 (m, 1H), 1.63-1.40 (m, 5H), 1.16-1.00 (m, 3H).

Intermediate 3

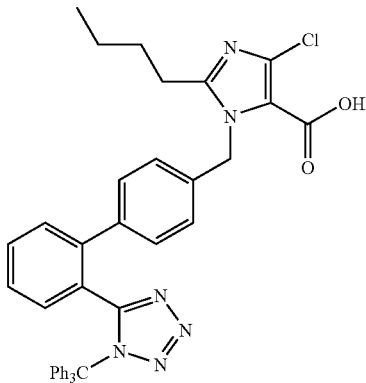

2-butyl-4-chloro-1-{[2'-(1-trityl-1H-tetrazol-5-yl) biphenyl-4-yl]methyl}-1H-imidazole-5-carboxylic acid Step A: 2-butyl-4-chloro-1-{[2'-(1H-tetrazol-5-yl) biphenyl-4-yl]methyl}-1H-imidazole-5-carboxylic acid (E3174)

Water (10 L) was added to a 22 L 4-neck round-bottom flask. The water was cooled to 0° C. At 0° C., potassium hydroxide (855 g, 15.24 mol) was added, followed by losartan potassium (500 g, 1.09 mol), sodium periodate (554 g, 2.59 mol) and ruthenium (III) chloride hydrate (12 g, 0.05 mol), and the reaction mixture was stirred at 0° C. overnight. The reaction mixture was filtered. Isopropanol (90 mL) was added to the filtrate while stirring. The solution was warmed to 25° C. and stirred for 2.5 hours. After 2.5 hours, phosphoric acid (1200 mL) was added, maintaining the temperature below 30° C. The mixture was stirred for 30 minutes and the product was filtered, washing with water. The residue was dried in the vacuum oven at 55° C. overnight. The solid was dissolved in methanol (4 L) and isopropyl acetate (12 L), and charcoal (activated carbon) (100 g) was added. The mixture was stirred at room temperature for 3.5 hours, filtered and concentrated. The product was redissolved in dichloromethane/methanol and precipitated with heptane to afford the title compound as a greenish brown foam, which was used in the subsequent step without further purification.

Step B: 2-butyl-4-chloro-1-{[2'-(1-trityl-1H-tetrazol-5-yl)biphenyl-4-yl]methyl}-1H-imidazole-5-carboxylic acid To a dichloromethane (4.5 L) solution of 2-butyl-4-chloro-1-{[2'-(1H-tetrazol-5-yl)biphenyl-4-yl]methyl}-1H-imidazole-5-carboxylic acid (235 g, 0.54 mol) was added triethylamine (85 mL, 0.59 mol), followed by a dichloromethane (800 mL) solution of trityl chloride (159 g, 0.56 mol), and the reaction mixture was stirred at room temperature overnight. The reaction mixture was washed with water, dried (magnesium sulfate), filtered, and concentrated under reduced pressure. Chromatography over silica eluting with 20-80% acetone/heptane afforded the title compound as an orange solid.

Intermediate 4

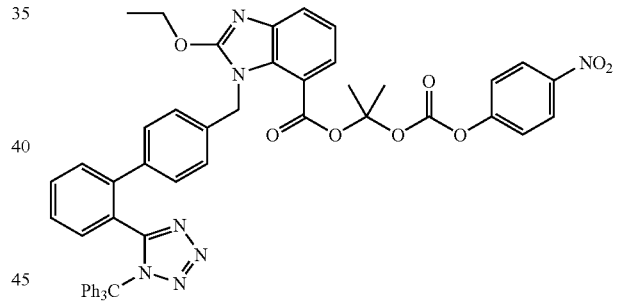

1-methyl-1-{[(4-nitrophenoxy)carbonyl]oxy}ethyl 2-ethoxy-1-{[2'-(1-trityl-1H-tetrazol-5-yl)biphenyl-4-yl]methyl}-1H-benzimidazole-7-carboxylate An orange suspension of mercuric oxide (1.17 g, 5.39 mmol) and 2-ethoxy-1-{[2'-(1-trityl-1H-tetrazol-5-yl)biphenyl-4-yl]methyl}-1H-benzimidazole-7-carboxylic acid (7.36 g, 10.8 mmol) in dry tetrahydrofuran (95 mL) was stirred at room temperature for 24 hrs. Then 2-chloroisopropyl p-nitrophenyl carbonate (prepared as described in U.S. Pat. No. 5,684,018) (1.40 g, 5.39 mmol) was added, and the reaction was stirred at room temperature for about 7 days and monitored by TLC (hexane/ethyl acetate 6/4). The mixture was diluted with dichloromethane, washed with water, and the organic layer was dried over sodium sulfate and concentrated under reduced pressure. The residue was purified by flash chromatography (Biotage SP1; column 65i; TLC method: n-hexane/ethyl acetate 7/3; $R_f$=0.20), affording the title product.

Example 1

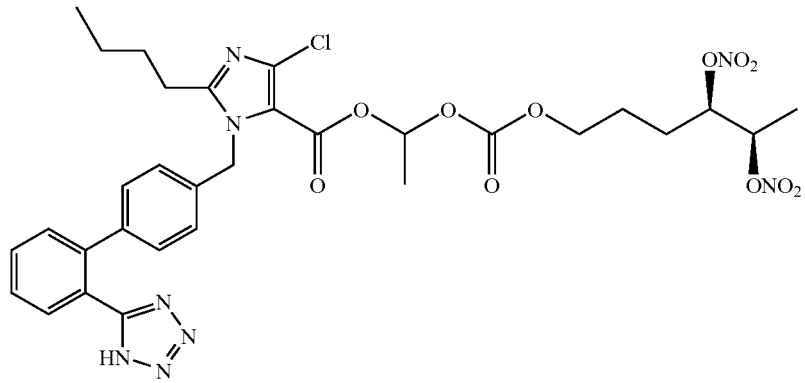

1-[({[(4R,5R)-4,5-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate

Step A: (4R,5R)-4,5-bis(nitrooxy)hexyl 1-chloroethyl carbonate

1-Chloroethyl chloroformate (1.55 mL, 14.2 mmol) was added dropwise to a stirred dichloromethane (50 mL) solution of (2R,3R)-6-hydroxyhexane-2,3-diyl dinitrate (intermediate 1, 2.60 g, 11.6 mmol), followed by pyridine (1.20 mL, 14.8 mmol). After 16 hours, the reaction mixture was concentrated in vacuo, and the residue was purified by column chromatography on silica gel, eluting with 5-25% ethyl acetate/hexanes to give the title compound as a colorless oil. $^1$H NMR (500 MHz, CDCl$_3$) δ 6.41 (q, J=5.7 Hz, 1H), 5.18-5.28 (m, 2H), 4.18-4.32 (m, 2H), 1.83 (d, J=5.7 Hz, 3H), 1.68-1.90 (m, 4H), 1.42 (d, J=6.4 Hz, 3H).

Step B: 1-[({[(4R,5R)-4,5-bis(nitrooxy)hexyl]oxy}carbonyl)oxy]ethyl 2-butyl-4-chloro-1-{[2'-(1-trityl-1H-tetrazol-5-yl)biphenyl-4-yl]methyl}-1H-imidazole-5-carboxylate A N,N-dimethylformamide (20 mL) solution of (4R,5R)-4,5-bis(nitrooxy)hexyl 1-chloroethyl carbonate (1.15 g, 3.48 mmol) was added to a stirred N,N-dimethylformamide (20 mL) suspension of 2-butyl-4-chloro-1-{[2'-(1-trityl-1H-tetrazol-5-yl)biphenyl-4-yl]methyl}-1H-imidazole-5-carboxylic acid (2.54 g, 3.74 mmol) and cesium carbonate (1.25 g, 3.84 mmol). The solution was stirred at 70° C. for 2 hours. Water (100 mL) was added, and the solution was extracted with ethyl acetate (3×100 mL). The combined organic layers were dried (magnesium sulfate), filtered, and concentrated in vacuo. The residue was purified by column chromatography on silica gel, eluting with 20-60% ethyl acetate/hexanes to give the title compound as a white solid. $^1$H NMR (500 MHz, CDCl$_3$) δ 7.90 (d, J=7.4 Hz, 1H), 7.49 (dt, J=1.4, 7.6 Hz, 1H), 7.45 (dt, J=1.1, 7.5 Hz, 1H), 7.31-7.36 (m, 4H), 7.26 (t, J=7.8 Hz, 6H), 7.10 (d, J=8.0 Hz, 6H), 6.93 (d, J=7.8 Hz, 2H), 6.86 (q, J=5.5 Hz, 1H), 6.79 (d, J=8.0 Hz, 2H), 5.54 (d, J=15.4 Hz, 1H), 5.32 (d, J=16.2 Hz, 1H), 5.14-5.24 (m, 2H), 4.10-4.20 (m, 2H), 2.50 (t, J=7.8 Hz, 2H), 1.7-1.9 (m, 4H), 1.62 (quintet, J=7.7 Hz, 2H), 1.54 (d, J=5.5 Hz, 3H), 1.37 (d, J=6.1 Hz, 3H), 1.27 (sextet, J=7.4 Hz, 2H), 0.85 (t, J=7.3 Hz, 3H).

Step C: 1-[({[(4R,5R)-4,5-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate A methanol (30 mL) suspension of 1-[({[(4R,5R)-4,5-bis(nitrooxy)hexyl]oxy}carbonyl)oxy]ethyl 2-butyl-4-chloro-1-{[2'-(1-trityl-1H-tetrazol-5-yl)biphenyl-4-yl]methyl}-1H-imidazole-5-carboxylate (1.63 g, 1.68 mmol) was heated to 70° C. for 2 hours. The reaction mixture was concentrated in vacuo, and the residue was purified by column chromatography on silica gel, eluting with 3-9% methanol/dichloromethane to give the title compound. $^1$H NMR (500 MHz, CD$_3$CN) δ 7.71 (dd, J=0.9, 7.8 Hz, 1H), 7.64 (dt, J=1.2, 7.6 Hz, 1H), 7.54 (dt, J=1.1, 7.6 Hz, 1H), 7.51 (d, J=7.5 Hz, 1H), 7.10 (d, J=8.2 Hz, 2H), 6.98 (d, J=8.0 Hz, 2H), 6.81 (q, J=5.5 Hz, 1H), 5.53 (d, J=16.7 Hz, 1H), 5.48 (d, J=17.1 Hz, 1H), 5.25-5.35 (m, 2H), 4.11 (t, J=5.8 Hz, 2H) 2.60 (t, J=7.7 Hz, 2H), 1.70-1.84 (m, 4H), 1.58 (quintet, J=7.6 Hz, 2H), 1.49 (d, J=5.5 Hz, 3H), 1.35 (d, J=6.3 Hz, 3H), 1.31 (sextet, J=7.5 Hz, 2H), 0.85 (t, J=7.4 Hz, 3H); LC-MS: m/z 731.3 (M+H).

Example 2

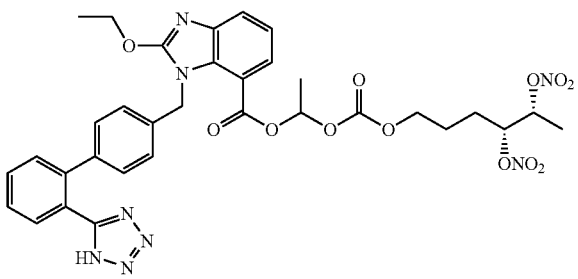

1-[({[(4R,5R)-4,5-bis(nitrooxy)hexyl]oxy}carbonyl)oxy]ethyl 2-ethoxy-1-{[2'-(1H-tetrazol-5-yl)biphenyl-4-yl]methyl}-1H-benzimidazole-7-carboxylate

Step A: (4R,5R)-4,5-bis(nitrooxy)hexyl 1-chloroethyl carbonate

1-Chloroethyl chloroformate (1.55 mL, 14.2 mmol) was added dropwise to a stirred dichloromethane (50 mL) solution of (2R,3R)-6-hydroxyhexane-2,3-diyl dinitrate (intermediate 1, 2.60 g, 11.6 mmol), followed by pyridine (1.20 mL, 14.8 mmol). After 16 hours, the reaction mixture was concentrated in vacuo, and the residue was purified by column chromatography on silica gel, eluting with 5-25% ethyl acetate/hexanes to give the title compound as a colorless oil. $^1$H NMR (500 MHz, CDCl$_3$) δ 6.41 (q, J=5.7 Hz, 1H), 5.18-5.28 (m, 2H), 4.18-4.32 (m, 2H), 1.83 (d, J=5.7 Hz, 3H), 1.68-1.90 (m, 4H), 1.42 (d, J=6.4 Hz, 3H).

Step B: 1-[({[(4R,5R)-4,5-bis(nitrooxy)hexyl]oxy}carbonyl)oxy]ethyl 2-ethoxy-1-{[2'-(1-trityl-1H-tetrazol-5-yl)biphenyl-4-yl]methyl}-1H-benzimidazole-7-carboxylate A N,N-dimethylformamide (20 mL) solution of (4R,5R)-4,5-bis(nitrooxy)hexyl 1-chloroethyl carbonate (2.94 g, 8.89 mmol) was added to a stirred N,N-dimethylformamide (20 mL) suspension of 2-ethoxy-1-{[2'-(1-trityl-1H-tetrazol-5-yl)biphenyl-4-yl]methyl}-1H-benzimidazole-7-carboxylic acid (7.46 g, 10.9 mmol) and cesium carbonate (3.95 g, 12.1 mmol). The solution was stirred at 70° C. for 2 hours. Water (100 mL) was added, and the solution was extracted with ethyl acetate (3×100 mL). The combined organic layers were dried (magnesium sulfate), filtered, and concentrated in vacuo. The residue was purified by column chromatography on silica gel, eluting with 20-60% ethyl acetate/hexanes to give the title compound as a white solid. $^1$H NMR (500 MHz, CDCl$_3$) δ 7.84 (dd, J=1.6, 7.3 Hz, 1H), 7.76 (dd, J=1.0, 7.9 Hz, 1H), 7.58 (dd, J=1.0, 7.9 Hz, 1H), 7.45 (dt, J=1.7, 7.4 Hz, 1H), 7.42 (dt, J=1.7, 7.4 Hz, 1H), 7.32 (t, J=7.4 Hz, 3H), 7.29 (dd, J=1.5, 7.4 Hz, 1H), 7.24 (t, J=7.8 Hz, 6H), 7.17 (t, J=7.9 Hz, 1H), 6.98 (d, J=8.2 Hz, 2H), 6.92 (d, J=8.2 Hz, 6H), 6.85 (q, J=5.4 Hz, 1H), 6.78 (d, J=8.2 Hz, 2H), 5.56 (s, 2H), 5.12-5.22 (m, 2H), 4.58-4.68 (m, 2H), 4.06-4.20 (m, 2H), 1.64-1.94 (m, 4H), 1.41-1.46 (m, 6H), 1.33 (d, J=6.4 Hz, 3H); LC-MS: m/z 999.5 (M+Na).

Step C: 1-[({[(4R,5R)-4,5-bis(nitrooxy)hexyl]oxy}carbonyl)oxy]ethyl 2-ethoxy-1-{[2'-(1H-tetrazol-5-yl)biphenyl-4-yl]methyl}-1H-benzimidazole-7-carboxylate A methanol (30 mL) suspension of 1-[({[(4R,5R)-4,5-bis(nitrooxy)hexyl]oxy}carbonyl)oxy]ethyl 2-ethoxy-1-{[2'-(1-trityl-1H-tetrazol-5-yl)biphenyl-4-yl]methyl}-1H-benzimidazole-7-carboxylate (2.47 g, 2.53 mmol) was heated to 70° C. for 2 hours. The reaction mixture was concentrated in vacuo, and the residue was purified by column chromatography on silica gel, eluting with 3-9% methanol/dichloromethane to give the title compound. $^1$H NMR (500 MHz, CD$_3$CN) δ 7.71 (d, J=7.6 Hz, 1H), 7.61 (dt, J=1.1, 7.6 Hz, 1H), 7.48-7.56 (m, 3H), 7.42 (d, J=7.6 Hz, 1H), 7.12 (t, J=7.9 Hz, 1H), 6.96 (d, J=8.3 Hz, 2H), 6.89 (d, J=8.2 Hz, 2H), 6.78 (q, J=5.4 Hz, 1H), 5.56 (d, J=16.7 Hz, 1H), 5.53 (d, J=16.7 Hz, 1H), 5.24-5.40 (m, 2H), 4.44-4.58 (m, 2H), 4.06-4.18 (m, 2H), 1.7-1.9 (m, 4H), 1.36-1.44 (m, 6H), 1.34 (d, J=6.2 Hz, 3H); LC-MS: m/z 735.3 (M+H).

Step D

The individual diastereomers of the title compound was separated by supercritical fluid chromatography (Chiralpak AD-H, 25% methanol/carbon dioxide), with diastereomer A the first in time to elute and diastereomer B the second in time to elute.

Diastereomer A:
$^1$H NMR (500 MHz, CD$_3$CN) δ 7.73 (dd, J=1.3, 7.7 Hz, 1H), 7.61 (dt, J=1.4, 7.7 Hz, 1H), 7.54 (dt, J=1.3, 7.6 Hz, 1H), 7.50 (dd, J=1.1, 7.9 Hz, 1H), 7.40 (dd, J=1.1, 7.8 Hz, 1H), 7.37 (dd, J=0.8, 7.9 Hz, 1H), 7.07 (t, J=7.9 Hz, 1H), 6.93 (d, J=8.5 Hz, 2H), 6.85 (d, J=8.2 Hz, 2H), 6.75 (q, J=5.4 Hz, 1H), 5.53 (s, 2H), 5.24-5.36 (m, 2H), 4.50 (qd, J=7.1, 10.2 Hz, 1H), 4.39 (qd, J=7.1, 10.2 Hz, 1H), 4.12 (t, J=6.0 Hz, 2H), 1.68-1.84 (m, 4H), 1.39 (t, J=7.0 Hz, 3H), 1.38 (d, J=5.4 Hz, 3H), 1.34 (d, J=6.4 Hz, 3H); LC-MS: m/z 735.3 (M+H).

Diastereomer B:
$^1$H NMR (500 MHz, CD$_3$CN) δ 7.70 (dd, J=1.1, 7.7 Hz, 1H), 7.61 (dt, J=1.4, 7.6 Hz, 1H), 7.58 (dd, J=0.9, 7.8 Hz, 1H), 7.50-7.56 (m, 2H), 7.44 (d, J=7.7 Hz, 1H), 7.15 (t, J=7.9 Hz, 1H), 6.99 (d, J=8.2 Hz, 2H), 6.91 (d, J=8.2 Hz, 2H), 6.80 (q, J=5.5 Hz, 1H), 5.55 (s, 2H), 5.24-5.36 (m, 2H), 4.50-4.60 (m, 2H), 4.08-4.18 (m, 2H), 1.70-1.84 (m, 4H), 1.44 (d, J=5.2 Hz, 3H), 1.42 (t, J=7.1 Hz, 3H), 1.34 (d, J=6.1 Hz, 3H); LC-MS: m/z 735.3 (M+H).

Example 3

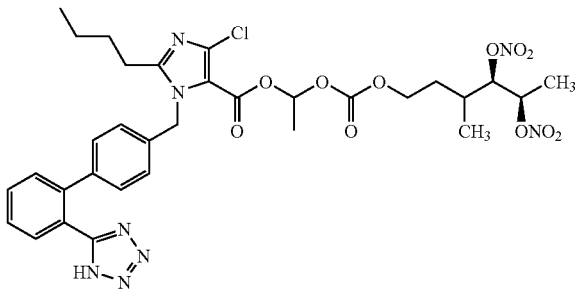

1-[({[(4R,5R)-3-methyl-4,5-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate Step A: (4R,5R)-3-methyl-4,5-bis(nitrooxy)hexyl 1-chloroethyl carbonate To a solution of (2R,3R)-6-hydroxy-4-methylhexane-2,3-diyl dinitrate (Intermediate 2, 0.78 g, 3.26 mmol) in CH$_2$Cl$_2$ (15 mL) cooled at 0° C., 1-chloroethyl chloroformate (0.355 mL, 3.26 mmol) was added. Then a solution of Pyridine (0.263 mL, 3.26 mmol) was added dropwise. The solution was stirred at room temperature overnight. Then it was diluted with CH$_2$Cl$_2$ (25 mL) and washed with HCl 1 N (2×15 mL), a saturated solution of NaHCO$_3$ (15 mL) and brine. The organic layer was dried over Na$_2$SO$_4$ and concentrated affording the title compound as colorless oil.
$^1$H NMR (300 MHz, DMSO-d6) δ 6.53-6.43 (m, 1H), 5.51-5.30 (m, 2H), 4.35-4.14 (m, 2H), 2.14-2.01 (m, 1H), 1.83-1.70 (m, 4H), 1.67-1.43 (m, 1H), 1.44-1.32 (m, 3H), 1.05-0.90 (m, 3H).

Step B: 1-[({[(4R,5R)-3-methyl-4,5-bis(nitrooxy)hexyl]oxy}carbonyl)oxy]ethyl 2-butyl-4-chloro-1-{[2'-(1-trityl-1H-tetrazol-5-yl)biphenyl-4-yl]methyl}-1H-imidazole-5-carboxylate (4R,5R))-3-methyl-4,5-bis(nitrooxy)hexyl 1-chloroethyl carbonate (1.01 g, 3.26 mmol) was added to a stirred solution of 2-butyl-4-chloro-1-{[2'-(1-trityl-1H-tetrazol-5-yl)biphenyl-4-yl]methyl}-1H-imidazole-5-carboxylic acid (Intermediate 3, 3.32 g, 4.88 mmol) and Cs$_2$CO$_3$ (2.40 g, 7.33 mmol) in DMF (18 mL). The solution was stirred at room temperature overnight. The mixture was diluted with a solution of NaH$_2$PO$_4$ 5% (40 mL) and extracted with EtOAc (3×25 mL). The organic layer was washed with water (4×20 mL) and brine. The residue was purified by flash chromatography (Biotage SP1, SNAP 100 g column, TLC method: n-Hexane/EtOAc 7:3, RE 0.45) affording the title compound that was used in the next step without any further characterization.

Step C: 1-[({[(4R,5R)-3-methyl-4,5-bis(nitrooxy) hexyl]oxy}carbonyl)oxy]ethyl 2-butyl-4-chloro-1-{[2'-(1H-tetrazol-5-yl)biphenyl-4-yl]methyl}-1H-imidazole-5-carboxylate 1-[({[(4R,5R)-3-methyl-4,5-bis(nitrooxy)hexyl]oxy}carbonyl)oxy]ethyl 2-butyl-4-chloro-1-{[2'-(1-trityl-1H-tetrazol-5-yl)biphenyl-4-yl]methyl}-1H-imidazole-5-carboxylate (1.08 g, 1.09 mmol) was dissolved in CH$_2$Cl$_2$ (3 mL) and MeOH was added (17 mL). The solution was heated in a microwave apparatus (70° C., 40 minutes). The solution was then concentrated and the residue was purified by flash chromatography (Biotage SP1, SNAP 100 g column, CH$_2$Cl$_2$/MeOH 98:2) affording the title compound.

$^1$H NMR (300 MHz, CDCl$_3$) δ 8.16 (d, 1H), 7.70-7.52 (m, 2H), 7.45 (d, 1H), 7.22 (d, 2H), 7.04 (d, 2H), 6.89 (q, 1H), 5.56 (s, 2H), 5.38-5.25 (m, 1H), 5.20-4.99 (m, 1H), 4.35-4.03 (m, 2H), 2.74 (t, 2H), 2.18-2.01 (m, 2H), 1.97-1.70 (m, 3H), 1.70-1.50 (m, 4H), 1.50-1.33 (m, 5H), 1.11-0.89 (m, 6H).

Example 4

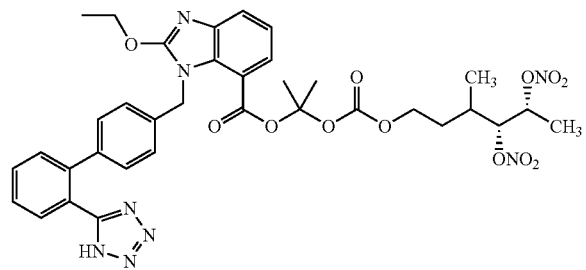

1-[({[(4R,5R)-3 Methyl-4,5-bis(nitrooxy)hexyl] oxy}carbonyl)oxy]-1-methylethyl 2-ethoxy-1-{[2'-(1H-tetrazol-5-yl)biphenyl-4-yl]methyl}-1H-benzimidazole-7-carboxylate Step A: 1-[({[(4R,5R)-3-Methyl-4,5-bis(nitrooxy) hexyl]oxy}carbonyl)oxy]-1-methylethyl 2-ethoxy-1-{[2'-(1-trityl-1H-tetrazol-5-yl)biphenyl-4-yl]methyl}-1H-benzimidazole-7-carboxylate (2R,3R)-6-hydroxy-4-methylhexane-2,3-diyl dinitrate (Intermediate 2, 0.78 g, 3.26 mmol) was added to a stirred solution of 1-methyl-1-{[(4-nitrophenoxy)carbonyl]oxy}ethyl 2-ethoxy-1-{[2'-(1-trityl-1H-tetrazol-5-yl)biphenyl-4-yl]methyl}-1H-benzimidazole-7-carboxylate (Intermediate 4, 1.96 g, 2.17 mmol) in CH$_2$Cl$_2$ (20 mL). The solution was stirred at room temperature overnight. The solution was diluted with CH$_2$Cl$_2$ (20 mL) washed with a solution of NaH$_2$PO$_4$ 5% (2×20 mL) and brine. The organic layers were dried over sodium sulfate and concentrated under reduced pressure. The residue was purified by flash chromatography (Biotage SP1, SNAP 100 g column, TLC method, n-Hexane/EtOAc 6:4, Rf:0.45) affording the title compound that was used without any further purification.

Step B: 1-[({[(4R,5R)-3 Methyl-4,5-bis(nitrooxy) hexyl]oxy}carbonyl)oxy]-1-methylethyl 2-ethoxy-1-{[2'-(1H-tetrazol-5-yl)biphenyl-4-yl]methyl}-1H-benzimidazole-7-carboxylate 1-[({[(4R,5R)-3-Methyl-4,5-bis(nitrooxy)hexyl]oxy}carbonyl)oxy]-1-methylethyl 2-ethoxy-1-{[2'-(1-trityl-1H-tetrazol-5-yl)biphenyl-4-yl]methyl}-1H-benzimidazole-7-carboxylate (1.77 g, 1.76 mmol) was dissolved in CH$_2$Cl$_2$ (5 mL) and MeOH was added (30 mL). After stirring at room temperature for 72 hrs, the solution was concentrated under reduced pressure. The residue was purified by flash chromatography (Biotage SP1, SNAP 100 g column, CH$_2$Cl$_2$/MeOH 98:2) affording the tile compound as a white solid.

$^1$H NMR (300 MHz, CD3OD) δ 8.04 (d, 1H), 7.64-7.59 (m, 2H), 7.53 (d, 1H), 7.32 (d, 1H), 6.92 (t, 1H), 6.87-6.74 (m, 3H), 6.69 (d, 1H), 5.62 (s, 2H), 5.38-5.22 (m, 1H), 5.15-5.00 (m, 1H), 4.39-3.96 (m, 4H), 2.16-1.97 (m, 1H), 1.94-1.70 (m, 1H), 1.65 (s, 6H), 1.49-1.31 (m, 6H), 1.02 (dd, 3H).

What is claimed is:

1. A compound having the structure

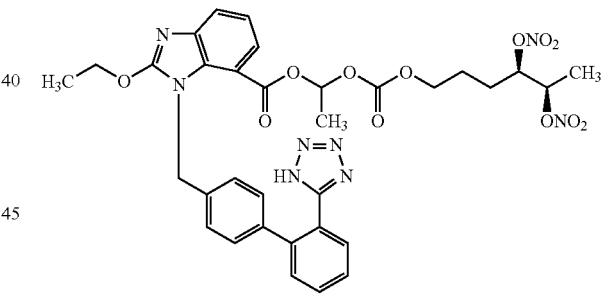

or a pharmaceutically acceptable salt thereof.

2. A pharmaceutical composition comprising a compound of claim 1 and a pharmaceutically acceptable carrier.

3. A pharmaceutical composition comprising a compound of claim 1, a diuretic, and a pharmaceutically acceptable carrier.

* * * * *